United States Patent [19]

Blanquaert

[11] Patent Number: 4,495,664
[45] Date of Patent: Jan. 29, 1985

[54] TITANIUM OR TITANIUM ALLOY PIN FOR CEMENT-FREE FIXING IN A LONG BONE TO FORM A PROSTHESIS

[75] Inventor: Daniel Blanquaert, Paris, France

[73] Assignee: Ceraver, Paris, France

[21] Appl. No.: 402,699

[22] Filed: Jul. 28, 1982

[30] Foreign Application Priority Data

Jul. 30, 1981 [FR] France .................... 81 14841

[51] Int. Cl.³ .......................... A61F 1/04; A61F 5/04
[52] U.S. Cl. ...................................... 3/1.913; 3/1.91; 128/92 C
[58] Field of Search ............ 128/92 C, 92 CA; 3/1.9, 3/1.91, 1.912, 1.913

[56] References Cited

U.S. PATENT DOCUMENTS

| | | | |
|---|---|---|---|
| 3,463,158 | 8/1969 | Schmitt et al. | 128/92 C |
| 4,038,703 | 8/1977 | Bokros | 3/1.5 |
| 4,261,063 | 4/1981 | Blanquaert | 3/1.91 |

FOREIGN PATENT DOCUMENTS

| | | | |
|---|---|---|---|
| 2628284 | 2/1977 | Fed. Rep. of Germany | 3/1.913 |
| 2827529 | 1/1980 | Fed. Rep. of Germany | 3/1.9 |

OTHER PUBLICATIONS

Alexander et al. "Carbon Polymer Composite for Tendons & Ligaments Repl" Trans, 4th Ann. Mtg. Soc. for Bio. Mat., 1978.

Primary Examiner—Richard J. Apley
Assistant Examiner—David J. Isabella
Attorney, Agent, or Firm—Sughrue, Mion, Zinn, Macpeak and Seas

[57] ABSTRACT

A titanium or titanium alloy pin for cement-free fixing in a long bone for a joint prosthesis or for bone repair is surrounded by a lattice of titanium wire with a mesh size of at least 0.3 mm. The central part of the pin and the lattice are coated with a coating of titanium oxide which protects them against long-term corrosion. The lattice is further coated with a biodegradable and biocompatible material having a low modulus of elasticity.

6 Claims, 3 Drawing Figures

TITANIUM OR TITANIUM ALLOY PIN FOR CEMENT-FREE FIXING IN A LONG BONE TO FORM A PROSTHESIS

The present invention concerns a pin of titanium or titanium alloy for cement-free fixing in a long bone to form a prosthesis of a joint or for bone repair, surrounded by a lattice of titanium wire with a mesh size of at least 0.3 mm, the pin and the lattice being coated with a coating of titanium oxide which protects them against long-term corrosion.

The pin provides for obtaining a composite lattice-bone structure having a modulus of elasticity close to that of the cortical bone tissue, free from the risk of long-term corrosion and favouring growth of bone tissue along its entire length. During the fitting of the pin into the medular duct of the long bone, the lattice may be damaged through the forced fitting of the pin which is necessary to lock it in position and to avoid any micromovement relative to the bone, this locking being difficult to achieve in view of anatomical differences between the bones concerned, even where a comprehensive range of pins of different sizes is available.

The objective of the present improvement is therefore to protect the lattice against such damage and to enable it to espouse the internal walls of the bone.

The pin in accordance with the invention is characterised in that the lattice is coated with a biodegradable and biocompatible material having a low modulus of elasticity.

For preference, the invention further consists in at least one of the following characteristics:

The biodegradable and biocompatible material is a copolymer of lactic acid and glycolic acid.

The biodegradable and biocompatible material is collagen.

The bidoegradable and biocompatible material contains added tricalcium phosphate.

The coating of the biodegradable and biocompatible material extends 0.3 to 1.5 mm beyond the envelope of the lattice.

In a pin for cement-free fixing in the upper part of the femur, the lattice is attached to the central part of the pin through the intermediary of thin transverse strips of titanium or titanium alloy disposed outside the metal lattice and welded to substantially plane lateral surfaces of the pin under a support ring which bears on the upper part of the femur after removal of its original head, and by means of a spot weld to the bottom point of the pin.

A pin for cement-free fixing in the upper part of the femur has shoulders on two opposite sides disposed in planes perpendicular to its axis, over its full height to a support ring which bears on the upper part of the femur after removal of its original head.

There will now be described, by way of example only and with reference to the accompanying drawing, a pin for cement-free fixing in the upper part of the femur to form a hip prosthesis:

The pin 1 comprises a support ring 2 which bears on the upper part of the femur after removal of its original head and a neck 3 terminating in a conical tenon 4 designed to be engaged in a spherical head (not shown).

Figure 1:
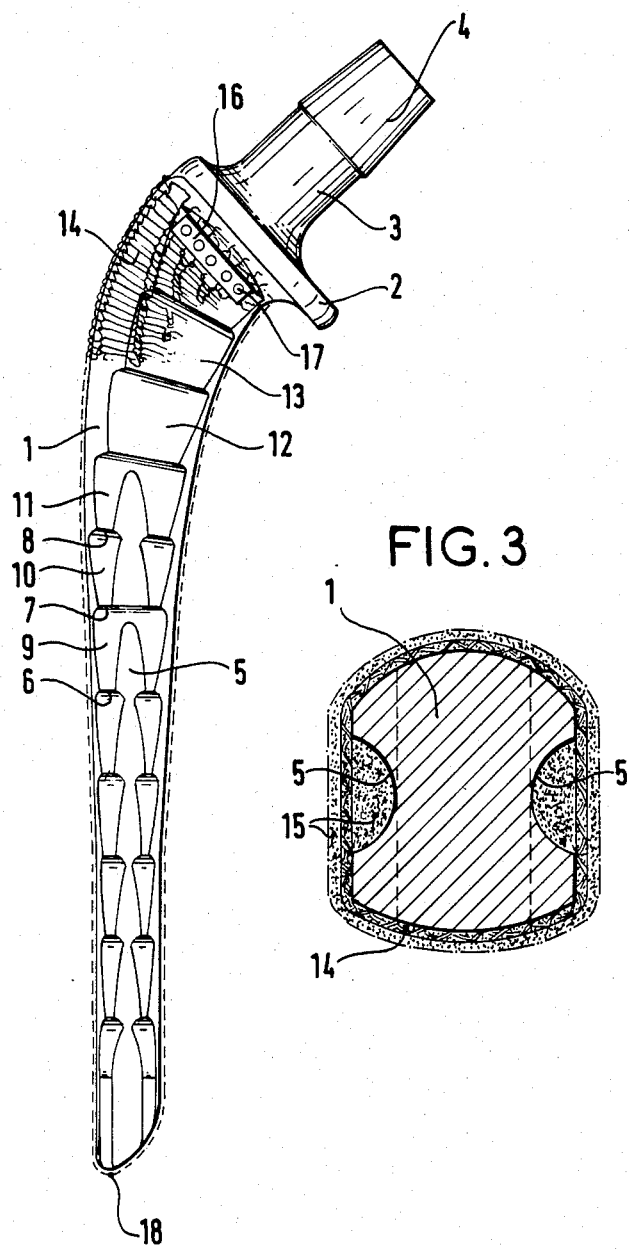
FIG. 1 shows the pin in side elevation, seen from the side comprising shoulders.
Figure 2:
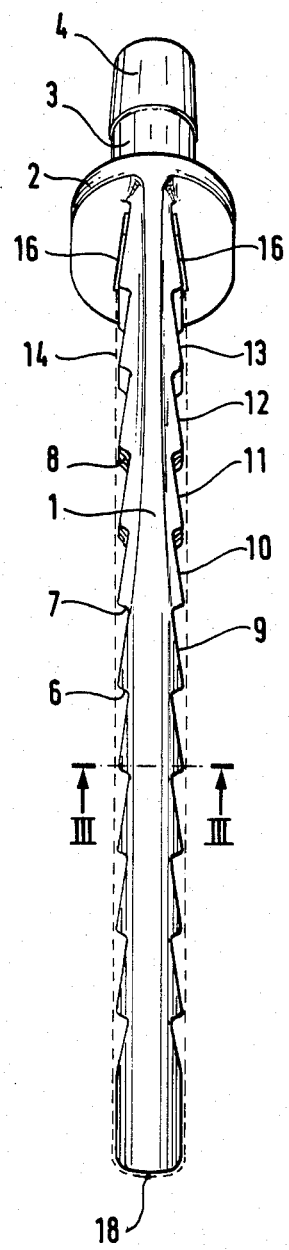
FIG. 2 shows the pin in side elevation, from the convex side of one of its other sides.
Figure 3:
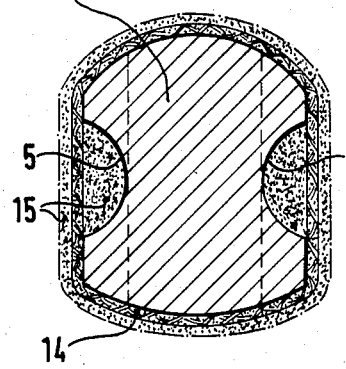
FIG. 3 is a transverse cross-section on the line III—III in FIG. 2.

Each lateral surface, seen in FIG. 1, comprises a central channel 5 over the greater part of its height and consecutive shoulders such as 6, 7, 8 giving it a double-sided fish-scale structure 9, 10, 11 and subsequently single-sided fish-scale structure 12, 13. It is surrounded with a lattice 14 of titanium wire coated with a biodegradable copolymer of lactic acid and glycolic acid or collagen designated 15 in FIG. 3. This lattice is designed so that on regrowth of bone tissue the modulus of elasticity of the composite lattice/bone material is similar to that of the existing bone.

The lattice of titanium wire is attached to the upper part of the central part of the pin by means of thin strips 16 spot-welded as at 17 by electron beam bombardment. It is also welded to the bottom point of the pin at 18.

The central part of the pin and lattice are of titanium or titanium alloy available under the designation TiAl6V4 containing 6% aluminium and 4% vanadium. They are coated with a coating of titanium oxide which protects them against long-term corrosion, formed by anodic oxidation.

Without departing from the scope of the invention, the pin may comprise on each side a number of lattice retaining strips and the spot welding of the lattice to the bottom end of the central part of the pin may be replaced with two vertical strips disposed on two opposite sides. A pin for fixing in a long bone other than the femur would naturally be of different shape.

I claim:

1. A pin of titanium or titanium alloy for cement-free fixing in a long bone to form a prosthesis of a joint or for bone repair, surrounded by a lattice of titanium wire with a mesh size of at least 0.3 mm, wherein said pin and said lattice are coated with a coating of titanium oxide which protects them against long-term corrosion, and said lattice is further coated with an outer coating of a biodegradable and biocompatible material having a low modulus of elasticity and wherein said coating of said biodegradable and biocompatible material extends 0.3 to 1.5 mm beyond the envelope of said lattice thereby protecting said lattice during the fitting of the pin into the bone repair site.

2. A pin according to claim 1, wherein said biodegradable and biocompatible material is a copolymer of lactic acid and glycolic acid.

3. A pin according to claim 1, wherein said biodegradable and biocompatible material is collagen.

4. A pin according to claim 1, wherein said biodegradable and biocompatible material contains added tricalcium phosphate.

5. A pin according to claim 1, for cement-free fixing in the upper part of the femur, wherein said lattice is at least partially attached to the central part of said pin through the intermediary of thin transverse strips of titanium or titanium alloy disposed outside said metal lattice and welded to substantially plane lateral surfaces of said central part of said pin under a support ring which bears on said upper part of the femur after removal of its original head, and by means of a spot weld to the bottom point of said pin.

6. A pin according to claim 1, for cement-free fixing in the upper part of the femur, wherein said pin has shoulders on two opposite sides disposed in planes perpendicular to its axis, over its full height and to a support ring which bears on said upper part of the femur after removal of its original head.

* * * * *